(12) United States Patent
Akiyama et al.

(10) Patent No.: US 6,240,786 B1
(45) Date of Patent: Jun. 5, 2001

(54) TWO-LAYER STRUCTURE COMPOSITE MATERIAL FOR DETECTING CRACKS

(75) Inventors: Morito Akiyama; Tadahiko Watanabe; Kazuhiro Nonaka, all of Tosu (JP)

(73) Assignee: Agency of Industrial Science and Technology, Tokyo (JP)

( * ) Notice: Subject to any disclaimer, the term of this patent is extended or adjusted under 35 U.S.C. 154(b) by 1114 days.

(21) Appl. No.: 08/705,063

(22) Filed: Aug. 29, 1996

Related U.S. Application Data

(63) Continuation of application No. 08/319,003, filed on Oct. 6, 1994, now abandoned.

(30) Foreign Application Priority Data

Oct. 6, 1993 (JP) .................................................... 5-276145

(51) Int. Cl.⁷ ........................................................ G01B 21/00
(52) U.S. Cl. .............................................. 73/799; 73/775
(58) Field of Search .............................. 73/774, 775, 799, 73/862.68, DIG. 4; 310/338

(56) References Cited

U.S. PATENT DOCUMENTS

| | | | |
|---|---|---|---|
| 3,603,142 | * 9/1971 | Saylak et al. ........................... | 73/799 |
| 4,255,974 | * 3/1981 | Dufrane et al. ......................... | 73/799 |
| 4,503,710 | * 3/1985 | Oertle et al. ............................ | 73/799 |
| 4,924,708 | * 5/1990 | Solomon et al. ....................... | 73/799 |
| 5,209,126 | * 5/1993 | Grahn ................................. | 73/862.68 |
| 5,349,869 | * 9/1994 | Diaz et al. .............................. | 73/799 |

* cited by examiner

*Primary Examiner*—Eric S. McCall
(74) *Attorney, Agent, or Firm*—Oblon, Spivak, McClelland, Maier & Neustadt, P.C.

(57) ABSTRACT

A two-layer structure composite material, by which it is possible to easily detect the occurrence of the cracks occurred in the structural material and to predict the possible destruction of the structural material before it actually occurs. To a structural material, a voltage generating material consisting of a ferroelectric material, a pyroelectric material or a piezoelectric material, is bonded to produce a two-layer structure material, and an electrode is provided for detecting voltage, which is generated owing to impact force.

7 Claims, 2 Drawing Sheets

TWO-LAYER STRUCTURE COMPOSITE MATERIAL FOR DETECTING CRACKS

This application is a Continuation-in-Part Continuation Division of application Ser. No. 08/319.003, filed on Oct. 6, 1994, now abandoned.

BACKGROUND OF THE INVENTION

1. Field of the Invention

The present invention relates to a two-layer structure composite material, comprising a piezoelectric material and a structural material, for detecting cracks in a structural material with the purpose of predicting destruction.

2. Description of Prior Art

Structural ceramic materials are fragile, and some treatment is needed when high reliability is required. In this respect, there are strong demands on a new type of ceramics, in which functional ceramics is combined with structural ceramics which generates a signal when cracks occur and contributes to the prediction of the possible destruction of the material before it actually occurs. Such the prediction of destruction is needed not only for structural ceramics but also for general structural materials, in which cracks may occur.

To detect cracks in structural materials, an acoustic emission method is normally used. In this case, it is necessary to set a large sensor on a structural material. However, in case sufficient space is not available to set the sensor, or in case a structural material is rotating at high speed, it is not possible to identify the occurrence of cracks and hense it is necessary for the prediction of possible destruction to disassemble and inspect a material at regular interval.

SUMMARY OF THE INVENTION

It is the object of the present invention to provide a two-layer structure composite material, by which it is possible to detect crack and to predict possible destruction before it actually occurs, and which can be used for a structural material with complicated shape, for a structural material with no additional space for providing a sensor or for a structural material in which the sensor cannot be mounted because it is rotating at high speed.

To attain the above object, a two-layer structure composite material comprises a structural material and a voltage generating material, which contains ferroelectric material, pyroelectric material or piezoelectric material. The voltage generating material is provided with an electrode to take out the generated voltage.

As the voltage generating materials, perovskite type, wurtzite type, ZnO type etc. are used. It is convenient to produce a two-layer structure of the structural material and piezoelectric material, it is advantageous because it can be used as an electrode for detecting cracks.

The above structural materials are combined with a ferroelectric material, a pyroelectric material or piezoelectric material, which generates voltage when impact force is applied. As such materials for generating voltage, perovskite type, wurtzite type or ZnO type materials are suited. As a perovskite type material, $ABO_3$ type ferroelectric materials can be used. As a wurtzite type material, AlN, GaN, InN, NbN or TaN may be used. As a ZnO structural material, ZnO and others may be used. Further, perovskite type materials may be mixed with resin or rubber and used. The ferroelectric materials must be used under Curie temperature.

To produce the two-layer structure composite material of the present invention, a structural material and a ferroelectric material or a piezoelectric material may be bonded together using an adhesive. Or, ferroelectric film or piezoelectric film may be generated on the structural materials using sol-gel method, CVD method, PVD method, etc.

The electrodes connected with the ferroelectric film or the piezoelectric film may be provided on both sides of the ferroelectric material or the pyroelectric material, or a comb type electrode may be provided on one side. As a result, the voltage generated owing to the occurrence of cracks can be easily detected. As described above, in case a conductive material is used as a structural material, it can be utilized as an electrode.

The two-layer structure composite material for detecting cracks thus obtained is used under such condition that a device for measuring and recording the generated voltage is connected with the electrode. When impact force is transmitted to the structural material, the force is propagated to the voltage generating material bonded to the structural material. Then, the occurrence of the cracks can be easily found by detecting the voltage using the measuring and recording device. Thus it is possible to predict the description of the structural material before it actually occurs.

DETAILED DESCRIPTION OF THE PREFERRED EMBODIMENTS

EXAMPLE 1

Figure 2:
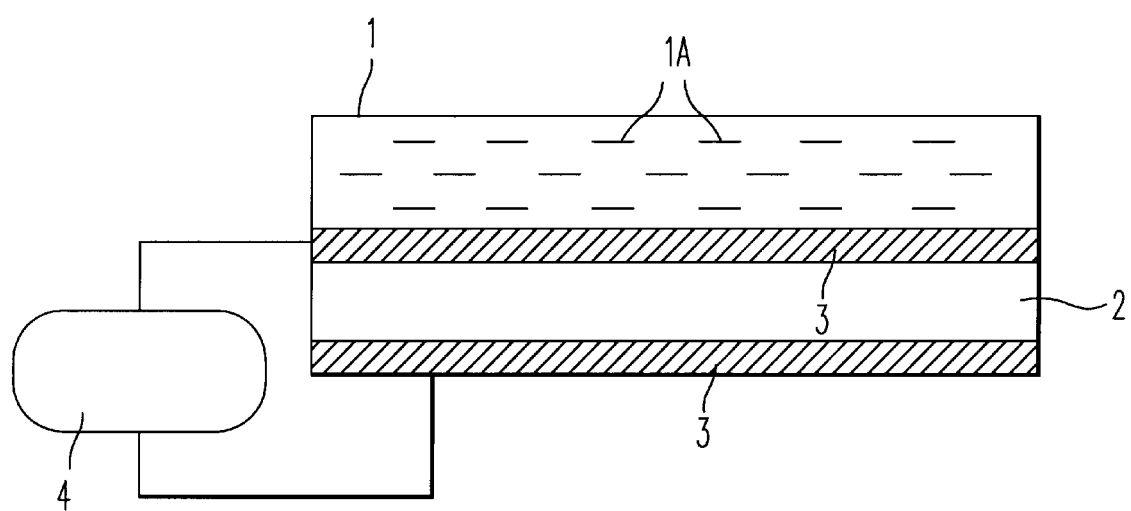
FIG. 2 is a sectional view diagrammatically showing the constitution of the two-layer structure composite material of the present invention.

Reference is now made to FIG. 2, where reference numerals 1 and 2 designate the structural material and the voltage generating material, respectively, which comprise the two-layer structure. A pair of electrodes 3, 3 for detecting generated voltage is illustrated on both sides of the voltage generating material 2. The structural material 1 may be a material reinforced by whiskers or fibers 1a. Reference numeral 4 designates the detector including a plotter for detecting and indicating the generated voltage between the above-mentioned electrodes 3, 3.

As a structural material 1, the conductive sintered material plate of $MoSi_2$—20% $Mo_2B_5$ of 2 mm in thickness was used. On the other hand, as a ferroelectric material, the PZT ($PbZr_{0.58}Ti_{0.42}$) plate 2 of 1 mm in thickness was employed. This PZT plate 2 was produced by polarization processing after baking Pt film for electrodes 3, 3 on both sides. This PZT plate was bonded to $MoSi_2$—20% $MoB_5$ sintered material plate with adhesive agent and the test piece of 12 mm in diameter was prepared, and this was placed on a metal base with the structural material 1 on it. A storage scope was connected with the structural material 1 and the electrode on the lower surface of the PZT plate 2 to measure the generated voltage, and this was recorded with a plotter 4.

Figure 1:
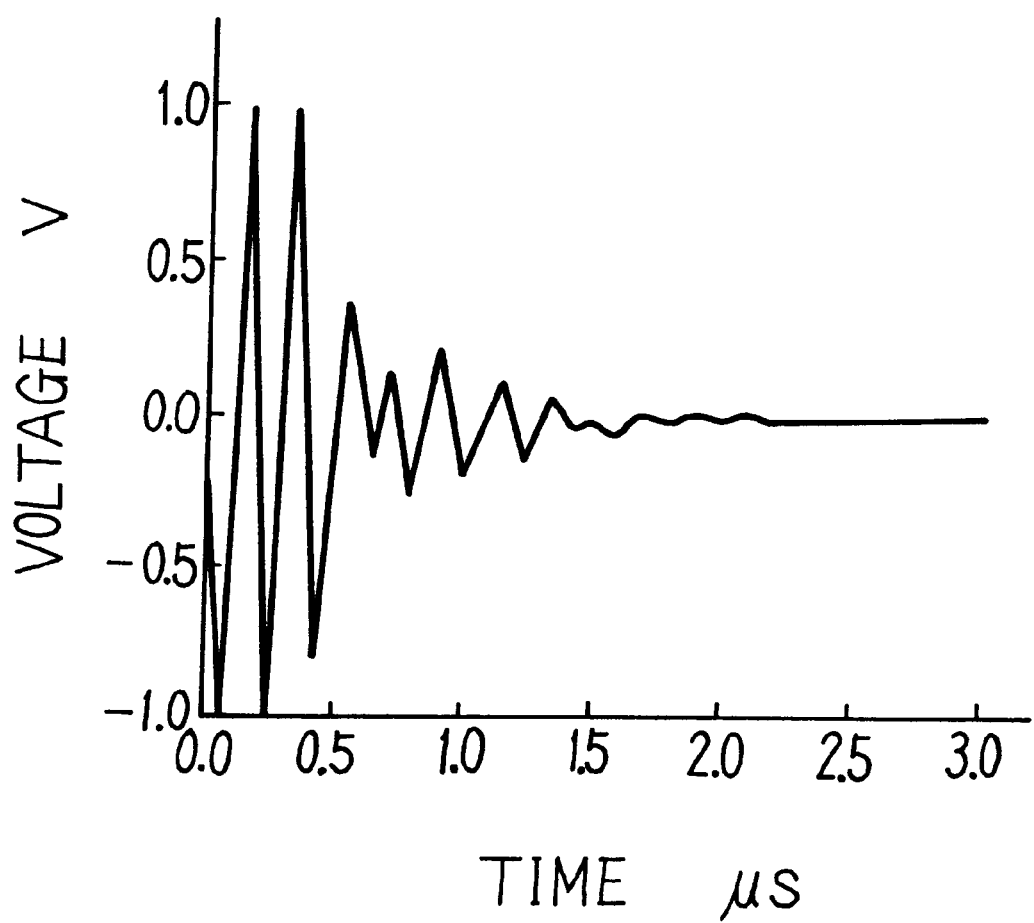
FIG. 1 represents the waveform diagram of voltage generated owing to the occurrence of cracks in the embodiment of the present invention.

On the mirror-polished surface of the $MoSi_2$—20% $MoB_5$ sintered material plate in the two-layer structure composite material placed on the metal base, a load of 196N was applied with a Vickers hardness tester to make an indentation, and cracks were generated from the corner of the indentation. As a result, the voltage signal corresponding to the occurrence of the crack was successfully obtained as shown in FIG. 1. Voltage also occured when the tip of the indenter was brought into the surface of the sintered material plate and when the indenter was impressed into the material. However, voltage in these cases was very weak compared with the case of FIG. 1, and hence the occurrence of cracks could be easily identified.

EXAMPLE 2

On the conductive $MoSi_2$—20% $MoB_5$ sintered material plate of 2 mm in thickness used as structural material, AlN thin film (1 μm in thickness) as a wurtzite material was prepared by sputtering method. Further, on the AlN thin film, Pt film was deposited as electrode. Using this as a test piece of 12 mm in diameter, this was placed on a metal base with structural material on it. A storage scope was connected with the structural material and the electrode deposited on AlN thin film prepared on it, and the generated voltage was measured and was recorded with a plotter.

On the mirror-polished surface of a $MoSi_2$—20% $MoB_5$ sintered material plate of the two-layer structure composite material placed on the metal base, the indentation was made with a Vickers hardness tester by the same procedure as in Example 1, and cracks were generated from the corner of the indentation. As a result, the voltage corresponding to the occurrence of the cracks was generated and similar to that of Example 1, and the occurrence of the cracks could be easily detected.

What we claim are:

1. A two-layer composite structure comprising:
   a structural material;
   a voltage generating material formed of a ferroelectric material, a pyroelectric material, or a piezoelectric material, which is bonded to said structural material and which generates a voltage in accordance with an impact force applied to said structural material; and
   an electrode, connected to said structural material and said voltage generating material, which detects cracks in said structural material by detecting said voltage generated by said voltage generating material.

2. A two-layer composite structure according to claim 1, wherein said structural material is a metal, a ceramic, or glass.

3. A two-layer composite structure according to claim 2, wherein said structural material is reinforced by ceramic fibers or whiskers.

4. A two-layer composite structure according to claim 1, wherein said structural material is a conductive ceramic material, and the voltage generating material is perovskite type, wurtzite type, or a ZnO type material.

5. A two-layer composite structure according to claim 4, wherein said structural material comprises a conductive ceramic material and is used as an electrode for detecting cracks.

6. A two-layer composite structure according to any of claims 1–5, wherein said structural material and said voltage generating material are bonded together via an adhesive agent.

7. A two-layer composite structure according to any of claims 1–5, wherein a thin film of said voltage generating material is bonded to said structural material.

* * * * *